(12) United States Patent
Ichikawa et al.

(10) Patent No.: US 10,478,057 B2
(45) Date of Patent: Nov. 19, 2019

(54) TESTING APPARATUS AND TESTING METHOD (71) Applicant: CHUKYO MEDICAL CO., INC., Nagoya-shi, Aichi (JP)

(72) Inventors: Kazuo Ichikawa, Nagoya (JP); Hiroyuki Sato, Nagoya (JP); Yoshiki Tanaka, Nagoya (JP)

(73) Assignee: CHUKYO MEDICAL CO., INC., Nagoya-shi (JP)

( * ) Notice: Subject to any disclaimer, the term of this patent is extended or adjusted under 35 U.S.C. 154(b) by 0 days.

(21) Appl. No.: 16/001,696

(22) Filed: Jun. 6, 2018

(65) Prior Publication Data

US 2019/0133439 A1 May 9, 2019

(30) Foreign Application Priority Data

Jun. 9, 2017 (JP) .................. 2017-114439

(51) Int. Cl.
*A61B 3/10* (2006.01)
*A61B 3/02* (2006.01)
*A61B 3/06* (2006.01)
*A61B 3/00* (2006.01)

(52) U.S. Cl.
CPC .............. *A61B 3/066* (2013.01); *A61B 3/005* (2013.01); *A61B 3/0033* (2013.01)

(58) Field of Classification Search
CPC ....... A61B 3/024; A61B 3/005; A61B 3/0041; A61B 3/18; A61B 3/0025; A61B 3/0033;

(Continued)

(56) References Cited

U.S. PATENT DOCUMENTS 6,260,970 B1 7/2001 Horn
6,290,357 B1 9/2001 Massengill et al.
(Continued)

FOREIGN PATENT DOCUMENTS

JP 2007-061416 A 3/2007
JP 5436712 B1 12/2014
(Continued)

OTHER PUBLICATIONS

Harwerth RS et al., "Progressive visual field defects from experimental glaucoma: measurements with white and colored stimuli," Optom Vis Sci. Aug. 1999;76(8):558-70.

(Continued)

*Primary Examiner* — Brandi N Thomas
(74) *Attorney, Agent, or Firm* — Ken I Yoshida (57) ABSTRACT

Provided are an apparatus and a method, for testing a visual function of a subject, that make it possible to appropriately test the sensitivity for each color for each region of a visual field. In a state in which the subject is caused to gaze at one point 6 in a background 7, a visual target 5 for testing a color-related visual function of the subject is displayed in a peripheral region of the gaze point 6 such that the luminance of the background 7 has a numerical value included between a numerical value smaller by 10% and a numerical value greater by 10% than the luminance of the visual target 5. Then, for each measurement point 300, a threshold that is a size of the visual target 5 that determines whether or not the subject can perceive the visual target 5 is obtained for a plurality of times.

8 Claims, 5 Drawing Sheets (58) Field of Classification Search
CPC ....... A61B 3/0058; A61B 3/066; A61B 3/102;
A61B 3/12; A61B 3/1225; A61B 3/14;
A61B 3/032; A61B 3/063; A61B 3/10;
A61B 3/1025; A61B 3/103; A61B 3/112;
A61B 5/14553; A61B 3/0075; A61B
3/0091; A61B 3/06
USPC ................ 351/200, 205–206, 209–211, 221,
351/243–246
See application file for complete search history.

(56) References Cited

U.S. PATENT DOCUMENTS

| | | | |
|---|---|---|---|
| 2015/0085258 A1 | 3/2015 | Ichikawa et al. | |
| 2016/0171741 A1 | 6/2016 | Stewart | |
| 2016/0262611 A1* | 9/2016 | Rotenstreich | A61B 3/14 |

FOREIGN PATENT DOCUMENTS

| | | |
|---|---|---|
| JP | 2016-144549 A | 8/2016 |
| WO | 2013/157573 A1 | 10/2013 |

OTHER PUBLICATIONS

Chris A. Johnson et al., "Blue-on-Yellow Perimetry Can Predict the Development of Glaucomatous Visual Field Loss," Arch Ophthalmol. 1993;111(5):645-650.

J M Wild et al., "The statistical interpretation of blue-on-yellow visual field loss," Investigative Ophthalmology & Visual Science Jun. 1995, vol. 36, 1398-1410.

* cited by examiner

TESTING APPARATUS AND TESTING METHOD

RELATED APPLICATIONS

This application claims the priority of Japanese Patent Application No. 2017-114439 filed on Jun. 9, 2017, which issued as Japanese Patent No. 6184046 on Aug. 4, 2017. The disclosure of the prior application is hereby incorporated herein in the entirety by reference.

BACKGROUND OF THE INVENTION

Field of the Invention

The invention relates to an apparatus and a method for testing a color-related visual function of a subject.

Description of Related Art

A large number of cone cells (S cone cells, M cone cells, and L cone cells) that perceive three colors of red, green, and blue, are arranged on the human retina, and thus the human visual function perceives various colors. Accordingly, an abnormality that a region cannot be perceived for a color while another region cannot be perceived for another color may occur in the human visual field as well. For this reason, the inventors have previously proposed a method that enables testing of a visual field for each color (color visual field) (see Japanese Patent No. 5436712). In the method proposed in Japanese Patent No. 5436712, a color-visual-field testing visual target (e.g., a grid) using a chromatic color is displayed, and the luminances of the visual target and the background at this time are set to be the same numerical value. This makes it possible to appropriately test the perception of color difference, rather than the perception of luminance difference.

SUMMARY OF THE INVENTION

Testing the degree (sensitivity for each color) indicating the ease of perception for each color in each region of a visual field is considered to be useful for early detection of eye diseases such as glaucoma. Japanese Patent No. 5436712 discloses that a grid is displayed as a visual target using a chromatic color, and whether the entire region of the grid can be normally perceived or a part of the region cannot be normally perceived, is tested. Proposing a method more suitable to obtain the sensitivity for each color for each region of a visual field than the test using a grid is beneficial for the detection of an eye disease that cannot be detected by the test using a grid.

Therefore, it is an object of the invention to provide an apparatus and a method that make it possible to appropriately test the sensitivity for each color for each region of a visual field.

In order to solve the above-described problems, a testing apparatus according to the invention includes a display means that displays, in a background, a visual target for testing a color-related visual function of a subject, the visual target and the background being displayed such that a luminance of the background has a numerical value included between a numerical value smaller by 10% and a numerical value greater by 10% than a luminance of the visual target; and a display control means that causes, in a state in which the subject is caused to gaze at a predefined point on the display means, the display means to display the visual target, while changing a size of the visual target, such that a threshold that is a size of the visual target that determines whether or not the subject can perceive the visual target is obtained in a peripheral region of a visual field center or at the visual field center.

According to the invention, in the state in which the subject is caused to gaze at a predefined point of the display means, the visual target is displayed in a peripheral region of the visual field center or at the visual field center, while changing the size of the visual target. Accordingly, it is possible to obtain a visual target size serving as a threshold determining whether or not the visual target can be perceived in the visual field region corresponding to the visual target. The threshold is correlated with the sensitivity for the color of the visual target. Specifically, the smaller the threshold is, the higher the sensitivity. Since the luminances of the visual target and the background are set to be similar, it is possible to appropriately test the perception of color difference rather than the perception of luminance difference.

According to the invention, the display control means switches between measurement points which are points at which the visual target is displayed, while displaying the visual target at one of the measurement points at each time point, and changes the size of the visual target for each of the measurement points.

By the visual target being displayed at one measurement point at each time point while switching the measurement points in this manner, it is possible to test the color sensitivity for each region of a visual field by a single test, and also to prevent the gaze point of the subject from moving toward the visual target.

According to the invention, the display control means repeats switching of the size of the visual target, using a point at which the visual target is displayed as a measurement point, such that a plurality of the thresholds can be obtained at the same measurement point. By obtaining a plurality of thresholds at the same measurement point in this manner, it is possible to accurately evaluate the color sensitivity at each measurement point.

According to the invention, the testing apparatus includes an input means through which the subject inputs a response indicating that the subject has been able to perceive the visual target. This facilitates determination as to which size of the visual target the subject has been able to perceive or has not been able to perceive, and hence facilitates obtainment of the threshold.

According to the invention, the display control means increases the size of the visual target if input of the response is absent, and decreases the size of the visual target if input of the response is present. By the testing apparatus automatically changing the visual target on the basis of the presence or absence of the response in this manner, it is possible to reduce the burden on a test practitioner and also facilitates obtainment of the threshold.

According to the invention, the display control means repeats switching of the size of the visual target until the number of times of switching from the presence to the absence or from the absence to the presence of the response reaches a predetermined number of two or more. This makes it possible to obtain a plurality (a predetermined number) of thresholds, and the color sensitivity can be accurately evaluated by obtaining the plurality of thresholds.

A testing method according to the invention includes presenting, in a state in which a subject is caused to gaze at one point in a background, a visual target for testing a color-related visual function of the subject, in a peripheral region of the gaze point or at the gaze point such that a luminance of the background has a numerical value included between a numerical value smaller than a luminance of the visual target by 10% and a numerical value greater than the luminance of the visual target by 10%; and requesting the subject for a response indicating that the subject has been able to perceive the visual target, and changing a size of the visual target in accordance with the presence or absence of the response, thereby obtaining a threshold that is a size of the visual target that determines whether or not the subject has been able to perceive the visual target. In addition, using a point at which the visual target is presented as a measurement point, measurement of the threshold is performed for a plurality of times for the same measurement point. This makes it possible to achieve the same effects as those achieved by the above-described testing apparatus according to the invention.

DESCRIPTION OF THE PREFERRED EMBODIMENTS

First Embodiment

Figure 1:
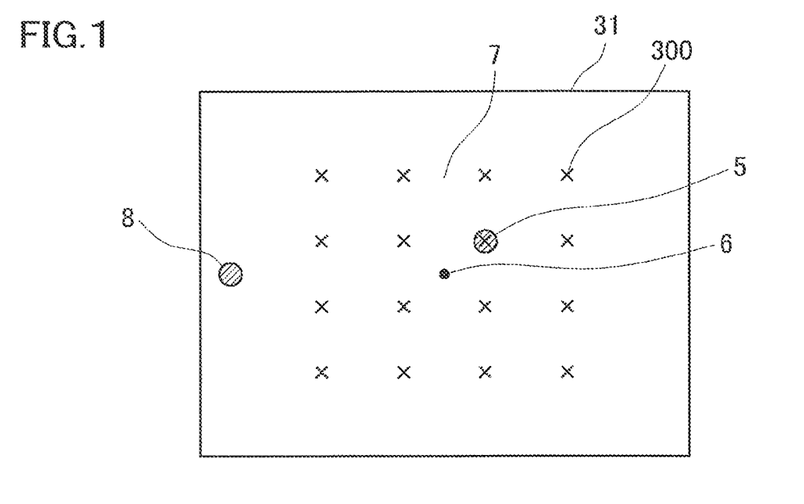
FIG. 1 is a diagram showing a test screen according to a first embodiment.

A first embodiment of the invention will be described below with reference to the drawings. In this embodiment, as shown in FIG. 1, in a state in which a subject is positioned in front of a screen 31, a reference point 6 is displayed on the screen 31, and the subject is caused to gaze at the reference point 6 with one eye. Then, a visual target 5 colored in a specific chromatic color is displayed in a peripheral region of a visual field center (reference point 6) of the subject gazing at the reference point 6. Then, with an elapse of time, the display position of the visual target 5 is randomly changed among a plurality of predefined measurement points 300. At this time, only one visual target 5 is displayed at each time point. While the visual target 5 is being displayed, the display position thereof is fixed at one of the measurement points 300. When the display position is changed from a measurement point 300 to another measurement point 300, the visual target 5 is temporarily turned off, and thereafter, the display position of the visual target 5 is changed.

FIG. 1 shows an example in which the number of measurement points 300 is 16. The 16 measurement points 300 are defined so as to be arranged in four columns by four rows centered at the reference point 6. For example, the intervals between the measurement points 300 are set such that, in a state in which the eye of the subject is spaced from the screen 31 by a predetermined distance (e.g., 30 cm), the visual angle between adjacent measurement points 300 is a predetermined angle (e.g., 1 degree).

Also, the subject is requested for a response indicating that the subject has been able to perceive the visual target 5. If the response is not present, the size of the visual target 5 is increased stepwise. On the other hand, if the response indicating that the subject has been able to perceive the visual target 5 is present, the size of the visual target 5 is decreased stepwise. Then, for each measurement point 300, the size change of the visual target 5 is repeated until the number of times of switching from the presence to the absence of the response, or from the absence to the presence of the response reaches a predetermined number (e.g., four). That is, for each measurement point 300, a visual target size that serves as a threshold determining whether or not the visual target 5 can be perceived is obtained for a predetermined number of times.

While the visual target 5 is being randomly displayed, a dummy visual target 8 is occasionally displayed at a blind spot position that cannot be perceived by the subject gazing at the reference point 6, instead of displaying the visual target 5. Then, if a response for the display of the dummy visual target 8 is received from the subject, it is determined that the subject's line of sight may be shifted from the reference point 6. Accordingly, it is determined that the reliability of the current test is low, and a test is performed again.

Furthermore, a background 7 of the screen 31 has a color (an achromatic color such as black, gray, or white) different from the color of the visual target 5, and the luminances of the visual target 5 and the background 7 are set to be similar (specifically, the luminance of the background 7 is included between a numerical value smaller by 10% and a numerical value greater by 10% than the luminance of the visual target 5). Here, a color having only the lightness attribute among the three attributes (lightness, saturation, and hue) of color is an achromatic color, and a color that is not the achromatic color is a chromatic color. The luminance of color refers to a Y value among tristimulus values of X, Y, and Z.

Figure 4:
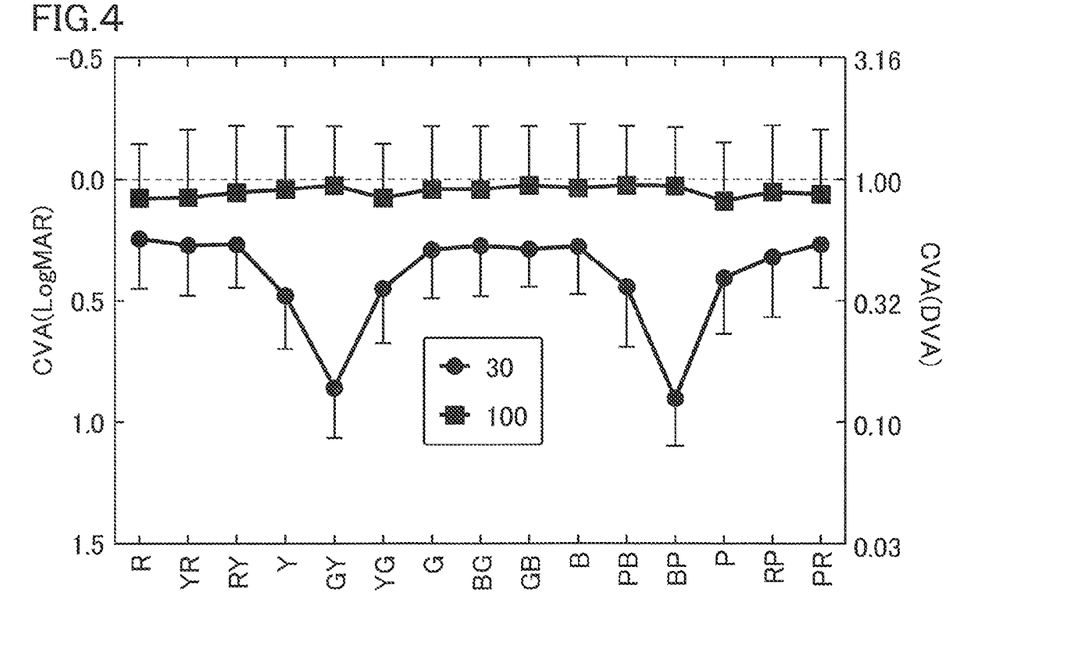
FIG. 4 is a diagram showing an example of testing results for color vision according to the background luminance.

FIG. 4 shows data on the basis of which the luminances of the visual target 5 and the background 7 are set to be similar. Specifically, FIG. 4 shows an example of measured results when color vision measurements for colors of red (R), yellowish red (YR), reddish yellow (RY), yellow (Y), greenish yellow (GY), yellowish green (YG), green (G), bluish green (BG), greenish blue (GB), blue (B), purplish blue (PB), bluish purple (BP), purple (P), reddish purple (RP), and purplish red (PR) were performed on a plurality of subjects. The horizontal axis indicates the colors, and the vertical axis indicates a logarithmic plot of the vision (the right vertical axis is an average value of the vision, and the left vertical axis is a standard deviation value of the vision).

The vision test was performed by coloring a Landolt ring with each of the colors indicated on the horizontal axis, and using a white point D65 as the background color. At this time, the luminance of the color of the Landolt ring was 30 candelas per square meter, and two different numbers of candelas per square meter, namely, 100 candelas and 30 candelas per square meter, were used for the luminance of the background color. A plot obtained when the luminance of the background color is 100 candelas per square meter and a plot obtained when the luminance of the background color is 30 candelas per square meter were shown on the upper side and the lower side, respectively, of the drawing.

As is evident from the drawing, the obtained results indicate that the visions for the various colors (color visions) are substantially the same when the luminance of the background color is 100 candelas per square meter, but the color visions for the colors are significantly different when the luminance of the background color is 30 candelas per square meter. Specifically, the color vision is relatively high for R (red), GB (greenish blue), and the like, and the colors in the vicinity thereof (the vicinity on a chromaticity diagram), whereas the color vision is relatively low for GY (greenish yellow) and BP (bluish purple), and the colors in the vicinity thereof. The luminances of the Landolt ring and the background are clearly different when the luminance of the background color is 100 candelas per square meter, and the Landolt ring and the background have an equal luminance when the luminance of the background color is 30 candelas per square meter.

Therefore, from the comparison between the results for the two cases, it can be considered that, when the luminance of the Landolt ring and the luminance of the background are clearly different, the subject recognizes the orientation of the Landolt ring by perceiving the luminance difference even if the subject cannot perceive the color difference between the Landolt ring and the background, and consequently, the color visions for the respective colors are substantially the same. In contrast, it can be considered that, when the luminance of the Landolt ring and the luminance of the background are the same, how well the subject perceives the color difference between the Landolt ring and the background is accurately reflected on the test results, and consequently, the color vision differs for each color.

It is clear that the applicable range of this finding, i.e., the finding that setting the luminances of the test visual target and the background to be similar is effective for testing of color vision, should not be limited to a color vision test, and the finding is considered to be also effective for testing of a color visual field. Therefore, this finding is also used for a visual function test according to this embodiment, and the luminances of the visual target 5 and the background 7 are set to be similar in FIG. 1.

As described above, in the test shown in FIG. 1, a visual target size (threshold) determining whether or not the visual target 5 can be perceived can be obtained for each measurement point 300. The threshold is correlated with the ease of perception (sensitivity) for the color of the visual target 5, and specifically, the smaller the threshold is, the higher the sensitivity is. That is, in the test shown in FIG. 1, the sensitivity for the color of the visual target 5 can be quantitatively tested for the visual field region corresponding to each measurement point 300. In addition, a plurality of thresholds determining whether or not the visual target 5 can be perceived can be obtained for each measurement point 300, so that the color sensitivity can be tested with reduced measurement errors, for example, by averaging the obtained plurality of thresholds.

The test shown in FIG. 1 is performed a plurality of times, and the color of the visual target 5 is changed among the plurality of tests. For example, the test shown in FIG. 1 may be performed for each of the 15 colors (red (R), yellowish red (YR), reddish yellow (RY), yellow (Y), greenish yellow (GY), yellowish green (YG), green (G), bluish green (BG), greenish blue (GB), blue (B), purplish blue (PB), bluish purple (BP), purple (P), reddish purple (RP), and purplish red (PR)) shown in the data in FIG. 4. The test shown in FIG. 1 may be performed for the three primary colors of light, namely, red, green, and blue, or may be performed for those colors, among the 15 colors in FIG. 4, that are particularly difficult to be perceived (specifically, GY and BP). The test shown in FIG. 1 is performed for each eye separately.

Figure 5:
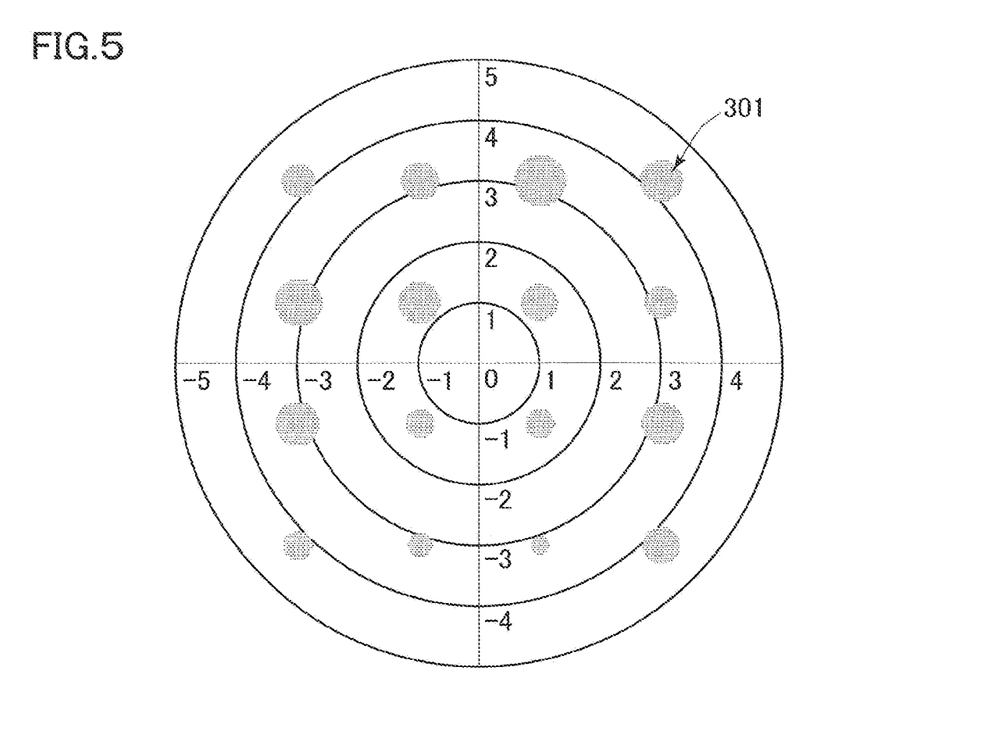
FIG. 5 is a diagram showing measurement points when a visual field test is actually performed.

On normal persons without any eye disease and persons with some eye abnormality, the inventors have performed tests (i.e., the same test as that shown in FIG. 1) for obtaining a visual target size (threshold) determining whether or not the visual target can be perceived, with some of the display points (measurement points) being varied. FIG. 5 shows measurement points 301 in the test. In FIG. 5, the unit of the values on the axes is a visual angle [°]. As shown in FIG. 5, the measurement points 301 are set at 16 positions having visual angles in the horizontal direction and the vertical direction of 1°, 3°, −1°, and −3°. As with the test shown in FIG. 1, the luminances of the visual target and the background are set to be similar, and the test was performed for a case when the color of the visual target was red and a case when the color of the visual target was bluish purple.

Figure 6A:
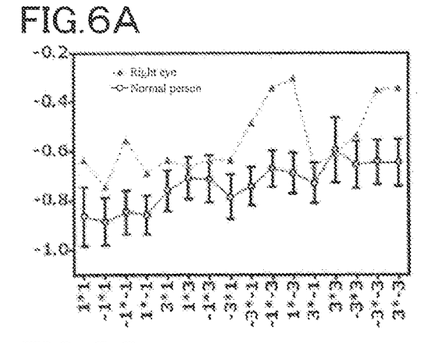
FIG. 6A is graph showing test result for the subject A when the color of a visual target is red.
Figure 6B:
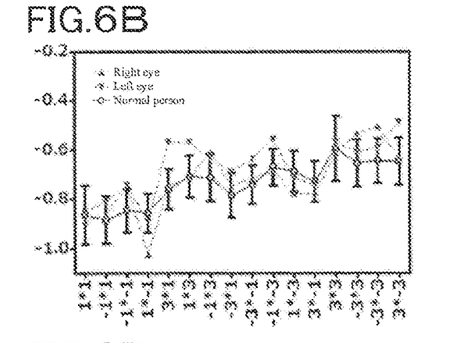
FIG. 6B is graph showing test result for the subject B when the color of a visual target is red.
Figure 6C:
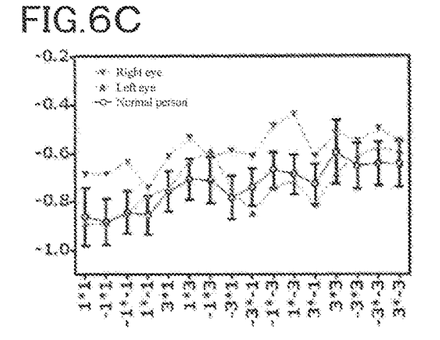
FIG. 6C is graph showing test result for the subject C when the color of a visual target is red.
Figure 6D:
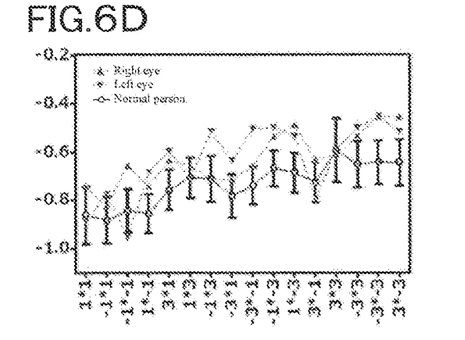
FIG. 6D is graph showing test result for the subject D when the color of a visual target is red.
Figure 7A:
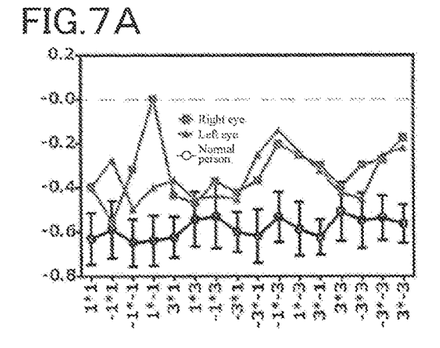
FIG. 7A is graph showing test result for the subject A when the color of a visual target is bluish purple.
Figure 7B:
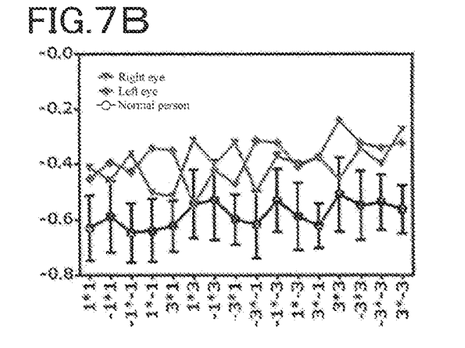
FIG. 7B is graph showing test result for the subject B when the color of a visual target is bluish purple.
Figure 7C:
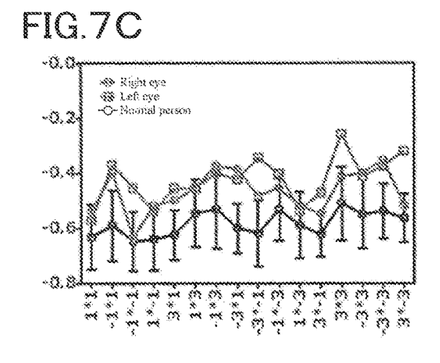
FIG. 7C is graph showing test result for the subject C when the color of a visual target is bluish purple.
Figure 7D:
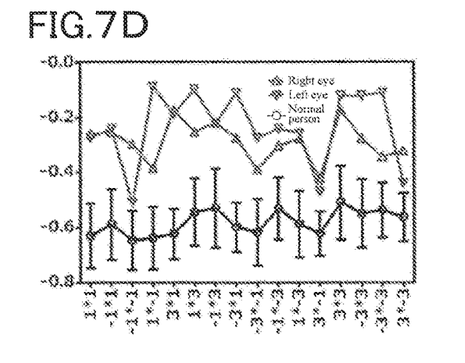
FIG. 7D is graph showing test result for the subject D when the color of a visual target is bluish purple.

FIGS. 6A, 6B, 6C, 6D, 7A, 7B, 7C and 7D show the test results. Specifically, FIGS. 6A, 6B, 6C, and 6D show the test results when the color of the visual target is red, and FIGS. 7A, 7B, 7C and 7D show the test results when the color of the visual target is bluish purple. FIGS. 6A, 6B, 6C, 6D, 7A, 7B, 7C and 7D show the results for four persons A, B, C, and D with some eye abnormality. Specifically, FIGS. 6A and 7A show the results for the person A. FIGS. 6B and 7B show the results for the person B. FIGS. 6C and 7C show the results for the person C. FIGS. 6D and 7D show the results for the person D. In FIGS. 6A, 6B, 6C, 6D, 7A, 7B, 7C and 7D, the horizontal axis indicates the position of the measurement point 301 (see FIG. 5) as [visual angle in the horizontal direction]*[visual angle in the vertical direction]. For example, "1*1" indicates the result at the measurement point 301 at which the visual angle in the horizontal direction is 1° and the visual angle in the vertical direction is 1° in FIG. 5. The vertical axes in FIGS. 6A, 6B, 6C, 6D, 7A, 7B, 7C and 7D represent the visual target size determining whether or not the visual target can be perceived, or in other words, thresholds. The threshold is larger toward the upper side of the axes. The result for the subject A in FIG. 6A shows the result for the right eye, and the results for the subjects B to D in FIGS. 6B, 6C, and 6D and the subjects A to D in FIGS. 7A, 7B, 7C and 7D show the results for the right eye and the left eye. In FIGS. 6A, 6B, 6C, 6D, 7A, 7B, 7C and 7D, the white circle point indicates an average value of the thresholds for the normal person.

As shown in FIGS. 6A, 6B, 6C, 6D, 7A, 7B, 7C and 7D, the test results indicate the tendency that the size of the visual target that can be perceived increases with an increase in the distance of the display points (measurement points 301 in FIG. 5) of the visual target to the visual field center, for both the normal person and the persons with some eye abnormality (e.g., glaucoma). However, the test results for the persons A to D with eye abnormality indicate a different tendency from the test result (white circle point) for the normal person, and specifically, indicate the tendency that, on the whole, the size of the visual target that can be perceived is larger than that indicated by the test result for the normal person. Both the normal person and the persons with eye abnormality show the tendency that even when the display points of the visual target are the same, the size of the visual target that can be perceived differs depending on the color difference. Specifically, they show the tendency that the size of the visual target that can be perceived is larger when the color of the visual target is bluish purple than when it is red. Furthermore, the results for the persons A to D with eye abnormality indicate that the variation of the thresholds caused by the changing display point of the visual target is larger as compared with that in the result for the normal person.

From the above-described test results, the test shown in FIG. 1 provides different test results between the normal person and the persons with an eye disease such as glaucoma, and it can be expected, for example, that visual field abnormality for each color can be detected at an early stage, an eye disease such as glaucoma can be detected at an early stage, and the degree of progress of the eye disease can be accurately diagnosed by investigating in advance the difference between the test result for the normal person and the test results for the persons with an eye disease, and the difference in the test results depending on each type of disease.

The conventional glaucoma tests include tests (tests using cross-sectional images of the retina) using a Humphrey perimeter or OCT (Optical Coherence Tomography images). A test using a Humphrey perimeter is performed as follows. That is, in a background irradiated with white light, white light having a higher intensity than the light of the background is emitted as a visual target. Then, the subject is caused to gaze at a reference point while the position and the brightness of the visual target are changed, and the subject is requested for a response indicating that the subject has been able to perceive the visual target. In terms of the detection of glaucoma, the OCT test can detect glaucoma earlier than the Humphrey visual field test. In the Humphrey visual field test, the visual target in white light is displayed in the background in white light. Accordingly, even when one of the types of cone cells (S cone cell, M cone cell, L cone cell) that perceive different colors has abnormality, the visual target can be perceived if the other cone cells are normal. From the foregoing, the Humphrey visual field test does not necessarily have a high accuracy as a glaucoma test.

In contrast, in the test shown in FIG. 1, the visual target 5 with a chromatic color and the background 7 are displayed so as to have similar luminances, whereby whether or not the visual target 5 can be perceived on the basis of color difference can be tested for each measurement point 300. When any of the three types of cones has abnormality, the presence of the abnormal cone can be known by performing a test using a visual target 5 with a color that can be easily perceived by the abnormal cone. This makes it possible to detect a visual field abnormality for each color and an eye disease such as glaucoma at an early stage, and accurately determine the degree of progress of the disease.

Figure 2:
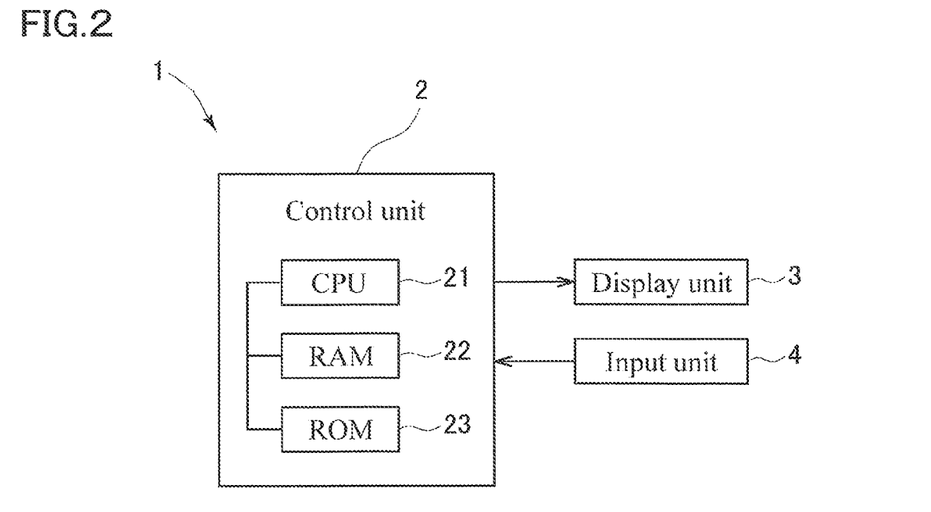
FIG. 2 is a block diagram of a testing apparatus.

The test shown in FIG. 1 is performed by using a testing apparatus 1 shown in FIG. 2. The testing apparatus 1 includes a display unit 3, an input unit 4, and a control unit 2 connected to the display unit 3 and the input unit 4. The display unit 3 includes, as with a liquid crystal display, for example, a portion (e.g., liquid crystal backlight) that emits light when being supplied with power. The display unit 3 includes the screen 31 that performs the display shown in FIG. 1. That is, the display unit 3 displays the visual target 5 in the background 7 of the screen 31, and displays the visual target 5 and the background 7 with similar luminances. Here, whether the luminance of the visual target 5 and the luminance of the background 7 are similar can be determined by measuring the luminances of the visual target 5 and the background 7 by using a spectral emission luminance meter or the like, and comparing the measured luminance value of the visual target 5 and the measured luminance value of the background 7. When the luminance of the visual target 5 and the luminance of the background 7 are different, the procedure of changing at least one of the luminance of the visual target 5 and the luminance of the background 7 and measuring the luminance again may be repeated until the luminance of the visual target 5 and the luminance of the background 7 become similar. Note that the display unit 3 may be any display such as a head mounted display as long as the luminances of the visual target 5 and the background 7 can be set to be similar. Note that the display unit 3 corresponds to the display means according to the invention.

The input unit 4 is configured as an operation unit that is operated by the subject, and constitutes a unit that performs input of a signal indicating that the subject has been able to perceive the visual target 5. The input unit 4 includes, for example, a grip portion that is gripped by the subject, and an operation unit that is pressed by the thumb of the subject in a state in which the subject is gripping the grip portion. Note that the input unit 4 corresponds to the input means according to the invention.

The control unit 2 has the same structure as that of a commonly used computer, and includes a CPU 21, a RAM 22, and a ROM 23. The CPU 21 executes various types of calculations, and the RAM 22 is a volatile storage unit that functions as a work area for the CPU 21. The ROM 23 is a nonvolatile storage unit that stores a program and data related to the invention. Note that the ROM 23 may be a nonvolatile storage unit in another form such as a hard disk.

Figure 3:
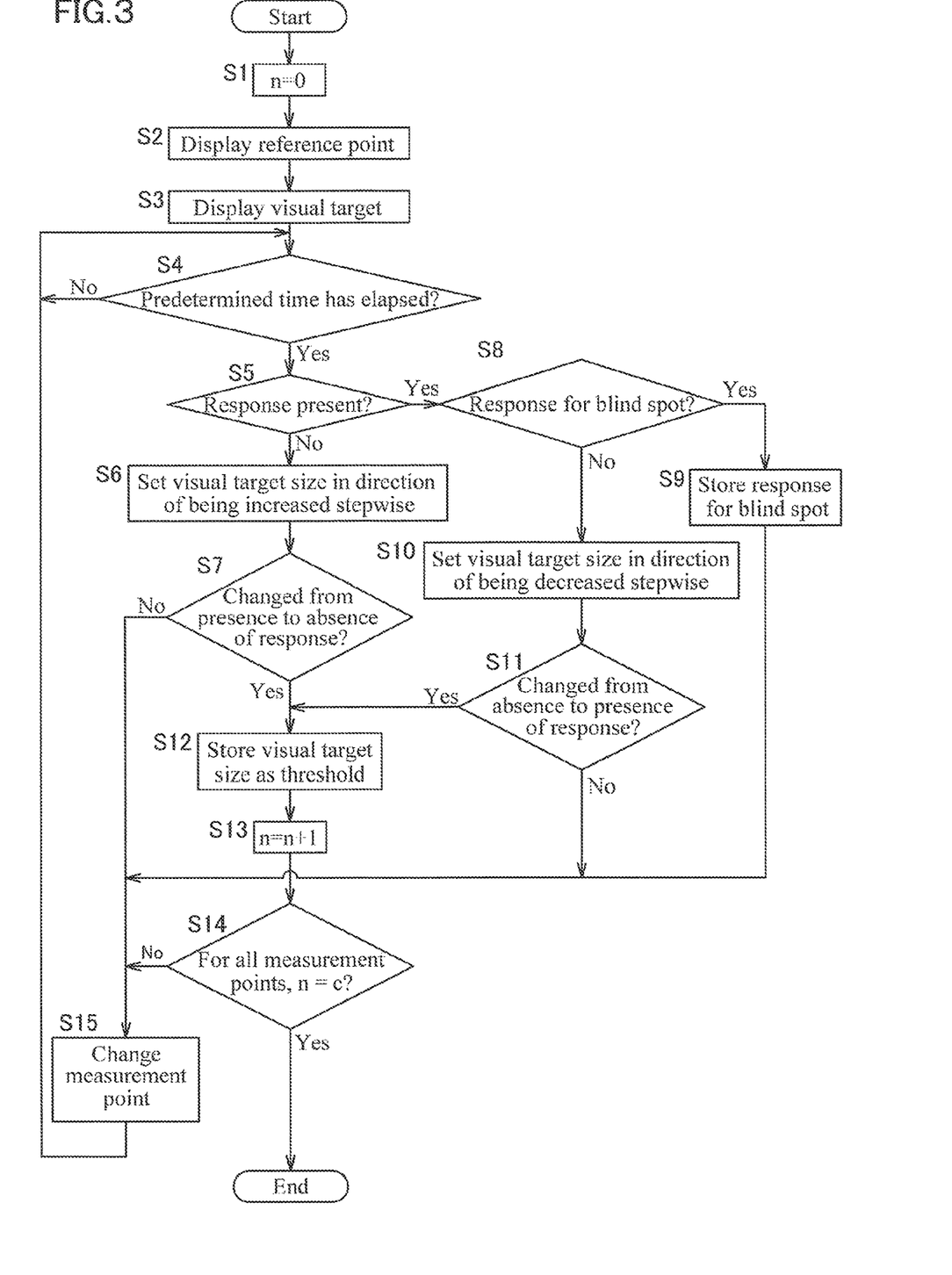
FIG. 3 is a flowchart illustrating processing (testing procedure) executed by a control unit.

The control unit 2 corresponds to the display control means according to the invention, and controls the display of the display unit 3, and acquires response signals from the input unit 4 to execute processing corresponding thereto. The processing executed by the control unit 2 will be described below with reference to FIG. 3. The processing shown in FIG. 3 is performed in a state in which the subject is positioned such that the eye of the subject is located at a predetermined distance (e.g., 30 cm) from the screen 31 of the display unit 3, and in which the input unit 4 is gripped by the subject. Note that the program for the processing shown in FIG. 3 is stored in the ROM 23.

Upon start of processing shown in FIG. 3, the control unit 2 (CPU 21) first sets a variable n, which indicates the number of measurements of a threshold that is a visual target size determining whether the visual target 5 can be perceived, to 0 (S1). The variable n is defined for each measurement point 300. In S1, each of the variables n of the measurement points 300 is set to 0. Next, as shown in FIG. 1, the reference point 6 is displayed at the center of the screen 31 (S2). The subject is caused to gaze at the reference point 6 with one eye.

Thereafter, the visual target 5 is randomly displayed in a peripheral region of the reference point 6 on the screen 31. More specifically, the visual target 5 is displayed on one of a plurality of measurement points 300 (S3). At this time, the visual target 5 and the background 7 are displayed such that the luminances of the visual target 5 and the background 7 are similar. Although the shape of the visual target 5 is not particularly limited, it is circular, for example. Although the initial size of the visual target 5 is not particularly limited, it is the smallest size of a plurality of predetermined levels of sizes, for example. The position at which the visual target 5 is initially displayed may be any one of the plurality of measurement points 300.

Next, it is determined whether the display time of the visual target 5 at the current measurement point 300 has elapsed a predetermined time (S4). As a precondition for this, the control unit 2 includes a timer inside, and the time elapsed from the start of the display of the visual target 5 at the current measurement point 300 (display time of the visual target 5) is measured by using the timer. When the display time of the visual target 5 has not reached the predetermined time (S4: No), the control unit 2 waits so as to allow the display of the visual target 5 at the current measurement point 300 to be continued.

If the display time of the visual target 5 has reached the predetermined time (S4: Yes), it is determined whether input of a response signal from the input unit 4 is present during display of the visual target 5 (S5). If such a response is not present (S5: No), the changing direction of the visual target size at the current measurement point 300 is set to a direction in which the visual target size is increased stepwise (S6). The set size changing direction (changing direction in which the visual target size is increased stepwise) is stored in the RAM 22 in association with the current measurement point 300.

Next, it is determined whether the response is present when the visual target 5 is previously displayed at the current measurement point 300 and the response is absent for the current display (S7). That is, it is determined whether there is a change from the presence of a response to the absence of a response, or a response was also absent for the previous display. If the response was previously present and is currently absent, or in other words, there is a change from the presence of the response to the absence of the response (S7: Yes), the current visual target size is stored as a threshold in the RAM 22 or the ROM 23 in association with the current measurement point 300 (S12). Then, the variable n at the current measurement point 300 is increased by 1 (S13). That is, n=n+1. Then, it is determined whether the variable n has reached a predetermined value C (C is an integer of 2 or more, for example, 4) for all the measurement points 300 (S14). If the variable n has reached the predetermined value C for all the measurement points 300 (S14: Yes), the processing shown in FIG. 3 ends. If the variable n has not reached the predetermined value C for even only one of the measurement points 300 (S14: No), the procedure proceeds to the processing of S15.

If it is determined in S7 that the response was also previously absent, or in other words, there is no change from the presence of the response to the absence of the response (the absence of the response is continued) (S7: No), the procedure proceeds to the processing of S15.

On the other hand, if it is determined in S5 that the response is present (S5: Yes), it is determined whether the response is a response to the dummy visual target 8 (see FIG. 1) displayed at a blind spot (S8). If the response is a response to the dummy visual target 8 (S8: Yes), a flag indicating that the response is present is turned on, or a variable indicating the number of the responses is increased by 1 and stored in the RAM 22 or the ROM 23 (S9). Then, the procedure proceeds to the processing of S15.

On the other hand, when the response is not a response to the dummy visual target 8, or in other words, is a response to the visual target 5 (S8: No), the changing direction of the visual target size at the current measurement point 300 is set to a direction in which the visual target size is decreased stepwise (S10). The set size changing direction (changing direction in which the visual target size is decreased stepwise) is stored in the RAM 22 in association with the current measurement point 300.

Next, it is determined whether the response was absent when the visual target 5 was previously displayed at the current measurement point 300 and whether the response is present for the current display (S11). That is, it is determined whether there is a change from the absence to the presence of the response, or the response was also present for the previous display. If the response was absent for the previous display and is present for the current display, or in other words, there is a change from the absence of a response to the presence of a response (S11: Yes), the current visual target size is stored as a threshold in the RAM 22 or the ROM 23 in association with the current measurement point 300 (S12). Then, the above-described processing of S13 and S14 is executed.

On the other hand, if it is determined in S11 that a response was also present for the previous display, or in other words, there is no change from the absence of a response to the presence of a response (the presence of the response is continued) (S11: No), the procedure proceeds to the processing of S15.

In the processing of S15, the display position of the visual target 5 is switched to another measurement point 300. At this time, in order to indicate that the display position of the visual target 5 is random, the switching is performed such that the display position of the visual target 5 is not switched between adjacent measurement points 300 before and after the switching, for example. In the processing of S15, the switching of the visual target 5 is performed while changing the size of the visual target 5 stepwise for each measurement point 300. Specifically, for each measurement point 300, the size (previous size) of the visual target 5 when the visual target 5 was previously displayed is stored in the RAM 22. As for the current display, the size of the visual target 5 is changed to a size one level larger or smaller than the stored previous size. At this time, when the display position is switched to a measurement point 300 at which the size changing direction has been set in the processing of S6 to the direction in which the visual target size is increased stepwise, the visual target 5 having a size one level larger than the previous size is displayed in the processing of S15. On the other hand, when the display position is switched to a measurement point 300 at which the size changing direction has been set in the processing of S10 to the direction in which the visual target size is decreased stepwise, the visual target 5 having a size one level smaller than the previous size is displayed in the processing of S15.

Since the response indicating that the subject has been able to perceive the visual target 5 is made for each measurement point 300, there is not a correlation in the size of the visual target 5 and in the size changing thereof between different measurement points 300. That is, assuming, for example, that the size of the visual target 5 is switched in 10 levels (the larger the number of the levels is, the larger the size is), even when the visual target 5 having a size of level 5 is previously displayed at a given measurement point 300 (first measurement point), and the size of the visual target 5 is increased by one level and the visual target 5 having a size of level 6 is currently displayed, the size of the visual target 5 may be decreased by one level and a visual target 5 having a size (e.g., a level 7) different from a level 5, which is the previous visual target size at the first measurement point, may be displayed at another measurement point 300 (second measurement point).

In the processing of S15, instead of displaying the visual target 5, the dummy visual target 8 (see FIG. 1) is occasionally displayed at a predefined blind spot position that cannot be perceived by the subject in a state in which the subject gazes at the reference point 6.

Even when the measurement point 300 is changed by the processing of S15, the luminances of the visual target 5 and the background 7 are not changed.

After S15, the procedure returns to S4, in which the above-described processing of S4 to S14 is executed for the switched measurement point 300.

Thus, in the processing shown in FIG. 3, each time the predetermined time has elapsed, the display position of the visual target 5 is randomly switched, and the visual target size is increased stepwise while the response is absent whereas the visual target size is decreased stepwise while the response is present, for each measurement point 300. Then, for each measurement point 300, a visual target size, with which switching is made from the absence to the presence of the response or switching is made from the presence to the absence of the response, is measured as a threshold, and the threshold measurement is performed for a predetermined number of times.

The control unit 2 outputs the measurement results (specifically, a predetermined number of thresholds for each measurement point 300) obtained through the processing shown in FIG. 3, by using a display means, a print means, or the like. The control unit 2 may output an average value of the predetermined number of thresholds, for example. The control unit 2 also outputs the presence or absence of a response for the dummy visual target 8, or the number of the responses. A test practitioner (e.g., a doctor) determines, for each color, the presence or absence of a region that is difficult to be viewed in each visual field, and determines the presence or absence and the degree of progress of an eye disease such as glaucoma, on the basis of the measurement results outputted from the testing apparatus 1. In addition, the test practitioner determines the reliability of the current test on the basis of, for example, the presence or absence of a response for the dummy visual target 8 and the number of responses, and performs a test again if the reliability is low.

As described above, according to this embodiment, after the luminances of the visual target 5 and the background 7 have been set to be similar, the visual target 5 with achromatic color is displayed in each region of a visual field while changing the size, and a visual target size determining whether or not the visual target 5 can be perceived is obtained as a threshold. Accordingly, it is possible to quantitatively and properly test the sensitivity (threshold) for each color in each region of a visual field. Since the visual target 5 is randomly displayed between a plurality of predefined measurement points 300, it is possible to prevent the subject from predicting where the visual target 5 is to be displayed. This makes it possible to prevent the gaze point of the subject from moving to the display position of the visual target 5, thereby inhibiting a reduction in the test reliability. Since a plurality of threshold measurements are performed for each measurement point 300 in this embodiment, the sensitivity for color can be evaluated with reduced measurement errors. Since whether the visual target size is to be increased or decreased is determined according to the presence or absence of a response using the input unit 4 in this embodiment, it is possible to shorten the time required to obtain a threshold.

Second Embodiment

Figure 8:
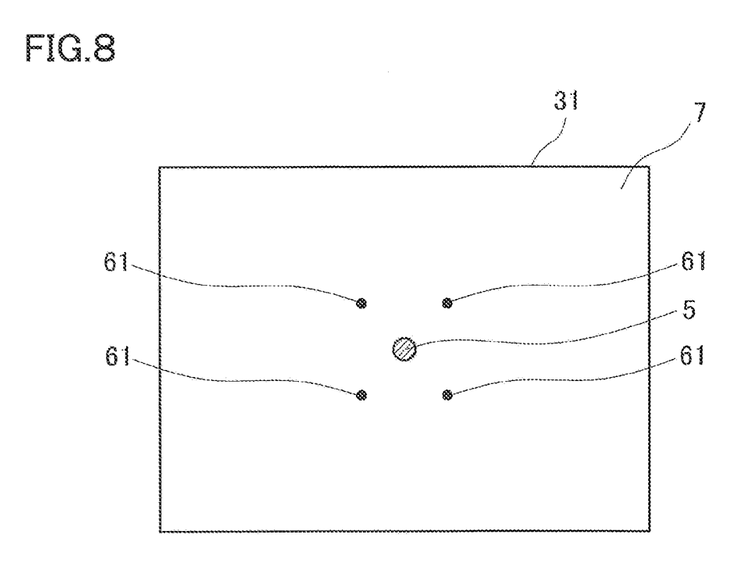
FIG. 8 is a diagram showing a test screen according to a second embodiment.

Next, a second embodiment of the invention will be described, focusing on differences from the above-described embodiment. As shown in FIG. 8, in this embodiment, a plurality of (in FIG. 8, four) points 61 are displayed so as to surround the center of the screen 31, and the subject is caused to gaze at a region surrounded by the points 61. Using the gaze region (center region) as a measurement point, a visual target 5 with a specific chromatic color is displayed in the gaze region. At this time, as with the first embodiment, the background 7 has a color (e.g., an achromatic color) different from the color of the visual target 5, and the luminances of the visual target 5 and the background 7 are set to be similar. Furthermore, the size of the visual target 5 is changed stepwise each time the predetermined time has elapsed. Specifically, if a response indicating that the subject has been able to perceive the visual target 5 is absent, the size of the visual target 5 is increased stepwise until it is determined that the response is present, whereas, if the response is present, the size of the visual target 5 is decreased stepwise until it is determined that the response is absent. That is, a threshold that is a size of the visual target 5 that determines whether or not the visual target 5 can be perceived is measured. Then, as with the first embodiment, this threshold measurement is performed a plurality of times (e.g., four times). Although the test shown in FIG. 8 is performed, for example, for colors (specifically, GY an BP) that are particularly difficult to be perceived among the 15 colors shown in FIG. 4, the test may be performed for other colors.

The test shown in FIG. 8 is performed by using the testing apparatus 1 shown in FIG. 2. At this time, in S2 in FIG. 3, the points 61 shown in FIG. 8 are displayed. In S3, the visual target 5 is displayed in the region surrounded by the points 61. In this embodiment, only one measurement point is present, and therefore, it is determined, in S14, whether the variable n has reached the predetermined value C for the measurement point at the center. In S15, the visual target size at the measurement point at the center is changed.

Thus, in this embodiment, it is possible to quantitatively and properly evaluate the sensitivity for each color (vision for each color) at the visual field center. On the basis of the sensitivity for each color at the visual field center, an eye disease such as glaucoma can be detected at an early stage, and the degree of progress of the disease can be accurately evaluated.

Other Embodiments

The invention is not limited to the above-described embodiments, and various modifications can be made without departing from the statements in the claims. For example, the first embodiment shows an example in which thresholds at various measurement points are measured in a concurrent manner by randomly displaying the visual target between a plurality of measurement points. However, the threshold measurement may be performed for each measurement point at a time. Specifically, a measurement point for which the threshold measurement is performed is selected from the plurality of measurement points, and the size of the visual target is changed stepwise at this measurement point (hereinafter referred to as a target measurement point). While the threshold measurement is being performed at the target measurement point, the visual target display and the threshold measurement are not performed for any other measurement point. Then, when the threshold measurement at the target measurement point ends, the target measurement point is switched to another measurement point, and thereafter, the threshold measurement is performed for the switched target measurement point. This procedure is repeated until a threshold has been obtained for all the measurement points.

In the first embodiment, whether the size of the visual target that is to be displayed next is to be increased or decreased is determined in accordance with the presence or absence of a response using the input unit 4. However, the visual target size may be changed step wise regardless of the presence or absence of a response. Specifically, at each measurement point, the size of the visual target is changed stepwise from the smallest size to the largest size, or from the largest size to the smallest size, and the presence or absence of a response during the changing is recorded. At this time, even when there is a change from the absence to the presence of the response, or from the presence to the absence of the response, the visual target size is changed to the largest size or to the smallest size without switching the changing direction thereof. This also makes it possible to obtain a threshold that is a visual target size with which switching of the presence and absence of the response occurs. Then, by performing the threshold measurement for a plurality of times for each measurement point, it is possible to obtain a plurality of thresholds for each measurement point. A single threshold measurement may be ended at a time point at which switching from the absence to the presence of the response occurs as the size of the visual target is increased stepwise from the smallest size at each measurement point (i.e., without being changed to the largest size), or at a time point at which switching from the presence to the absence of the response occurs as the size of the visual target is decreased stepwise from the largest size (i.e., without being changed to the smallest size). This also makes it possible to obtain a threshold.

When the threshold measurement is performed for each measurement point at a time, or when the threshold measurement is performed at the visual field center in the second embodiment, the visual target may be continuously displayed while the visual target size is being switched. That is, while constantly displaying the visual target, the size change of the visual target may be performed such that the size of the visual target is gradually increased while the response is absent, and the size of the visual target is gradually decreased while the response is present.

Although the example in FIG. 1 shows a case where the number of measurement points is 16, the number of measurement points may be a number other than 16. Although the above embodiments show a circular visual target as an example, the visual target may be polygonal (square), oval, or the like, or may be a pattern, a design (e.g., an animal, a plant, or food), or the like. A pattern, a design, or the like is particularly preferable when the subject is a child.

The above embodiments show examples in which the visual target with a chromatic color is displayed, however, a visual target with an achromatic color may be displayed. In this case, it is possible to measure the color sensitivity for an achromatic color. The background may have either an achromatic color or a chromatic color as long as the color is different from that of the visual target.

Although the above embodiments show examples in which the display point of the visual target is automatically switched by the control unit, it is possible to adopt a configuration in which a test practitioner (e.g., a doctor) can select the display point and the switching timing of the visual target. The subject may provide a verbal response indicating that the subject has been able to perceive the visual target.

DESCRIPTION OF THE REFERENCE CHARACTERS

1 testing apparatus
2 control unit (display control means)
3 display unit (display means)
31 screen of display unit
4 input unit (input means)
5 visual target
6 reference point
7 background
8 dummy visual target
300 measurement point

What is claimed is:

1. A testing apparatus comprising:
a display means that displays, in a background, a visual target varying in size and color for testing a color-related visual function of a subject, the visual target and the background being displayed such that a luminance of the background has a substantially same numerical value in luminance of the visual target;
a display control means that causes, in a state in which the subject is caused to gaze at a predefined point on the display means, the display means to display the visual target, while changing a size of the visual target, such that a threshold that is a size of the visual target that determines whether or not the subject can perceive the visual target is obtained in a peripheral region of a visual field center or at the visual field center; and
a obtaining means for obtaining at least one of the threshold in the size of the visual target that determines whether or not the subject can perceive the visual target as displayed in one of a predetermined set of colors over the background whose luminance value is substantially the same as the luminance of the visual target.

2. The testing apparatus according to claim 1, wherein the display control means switches between measurement points which are points at which the visual target is displayed, while displaying the visual target at one of the measurement points at each time point, and changes the size of the visual target for each of the measurement points.

3. The testing apparatus according to claim 1, wherein the display control means repeats switching of the size of the visual target, using a point at which the visual target is displayed as a measurement point, such that a plurality of the thresholds can be obtained at the same measurement point.

4. The testing apparatus according to claim 1, comprising an input means through which the subject inputs a response indicating that the subject has been able to perceive the visual target.

5. The testing apparatus according to claim 4, wherein the display control means increases the size of the visual target if input of the response is absent, and decreases the size of the visual target if input of the response is present.

6. The testing apparatus according to claim 5, wherein the display control means repeats switching of the size of the visual target until the number of times of switching from the presence to the absence or from the absence to the presence of the response reaches a predetermined number of two or more.

7. A testing method comprising:
presenting, in a state in which a subject is caused to gaze at one point in a background, a visual target varying in size and color for testing a color-related visual function of the subject, in a peripheral region of the gaze point or at the gaze point such that a luminance of the background has a substantially same numerical value in luminance of the visual target;

requesting the subject for a response indicating that the subject has been able to perceive the visual target as a size of the visual target is changed in accordance with the presence or absence of the response;

thereby obtaining a threshold that is a size of the visual target that determines whether or not the subject has been able to perceive the visual target; and repeating the presenting, requesting and obtaining steps as the visual target is displayed in another one of a predetermined set of colors.

8. The testing method according to claim 7, wherein using a point at which the visual target is presented as a measurement point, measurement of the threshold is performed for a plurality of times for the same measurement point.

* * * * *